United States Patent [19]

Reese et al.

[11] 4,238,471

[45] Dec. 9, 1980

[54] ASSAY FOR THYROID HORMONE BINDING CAPACITY

[75] Inventors: Max G. Reese; LaVell R. Johnson, both of Salt Lake City, Utah

[73] Assignee: Becton, Dickinson and Company, Paramus, N.J.

[21] Appl. No.: 923,712

[22] Filed: Jul. 12, 1978

[51] Int. Cl.$^3$ .................... G01N 33/16; B01J 1/22; G21H 5/02

[52] U.S. Cl. .................... 424/1; 23/230 B; 424/12

[58] Field of Search .................... 424/1; 23/230 B, 283

[56] References Cited

U.S. PATENT DOCUMENTS

| | | | |
|---|---|---|---|
| 3,896,217 | 7/1975 | Johnson | 424/1 |
| 3,941,564 | 3/1976 | Fader et al. | 23/230 B |
| 4,039,652 | 8/1977 | Adams et al. | 424/1 |
| 4,108,976 | 8/1978 | Reese | 424/1 |
| 4,110,076 | 8/1978 | Margher et al. | 23/230.6 |
| 4,125,375 | 11/1978 | Hunter | 23/230 B |
| 4,128,628 | 12/1978 | Brooker et al. | 424/1 |

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

Automated assay for qualitative determination of thyroid hormone binding capacity of a serum sample in which serum and $T_3$ tracer are caused to flow through a chamber containing a $T_3$ binder supported on a solid support. The amount of $T_3$ tracer which passes through the chamber, and the amount of $T_3$ tracer bound to the binder in the chamber are determined to thereby determine the percent of bound $T_3$ tracer. Such percent is then compared with the percent of $T_3$ tracer bound in a referenced sample to qualitatively determine the $T_3$ binding capacity of the serum sample.

5 Claims, No Drawings

ASSAY FOR THYROID HORMONE BINDING CAPACITY

The present invention relates to an assay, and more particularly to an assay for qualitatively determining the thyroid hormone binding capacity of a serum sample.

Human serum contains proteins which are known to bind thyroid hormones; in particular, thyroxine binding globulin (TBG), thyroxine binding prealbumin (TBPA) and albumin. The thyroid hormones (thyroxine ($T_4$) and triiodothyronine ($T_3$)) are primarily bound to TBG.

A qualitative determination of changes in the concentration of the thyroid hormone binding capacity; in particular, TBG, is useful in evaluating various factors; e.g., hypothyroidism, the effect on TBG resulting from pregnancy, estrogen administration, etc.

In accordance with the present invention, there is provided an automated assay for qualitative determination of the thyroid hormone binding capacity of a serum in which a $T_3$ tracer is mixed with an unknown serum sample and caused to flow through a chamber containing a $T_3$ binder supported on a solid support. The amount of $T_3$ tracer which passes through the chamber is determined, followed by flowing an eluting solution through the chamber to release any $T_3$ tracer which is bound to the binder in the chamber. The amount of $T_3$ tracer released from the binder is determined, to thereby determine the percent of $T_3$ tracer present in the serum sample which was bound to the binder in the chamber. The percent of $T_3$ tracer bound in the sample is compared with the percent of $T_3$ tracer bound in a reference sample to determine the difference in $T_3$ binding capacity between the sample and the reference sample to thereby qualitatively determine the $T_3$ binding capacity of the serum sample.

The binder or receptor which is bound to the solid support may be any one of a wide variety of thyroid hormone binders, including antibodies, serum proteins and the like. The preferred binder is an antibody.

The $T_3$ tracer may be any one of a wide variety of tracers in which $T_3$ or appropriate analog thereof includes a "label" or "tag", such as a radioactive isotope, enzyme, fluoroescent tag, etc. The preferred tracer includes a radioactive isotope as the label or tag, and in particular a radioiodine tag.

The binder may be covalently bound to a suitable support, as described in U.S. Pat. No. 4,059,685 or U.S. Application Ser. No. 774,277, filed on Mar. 4, 1977, which are both hereby incorporated by reference. As described in such applications, the particulate support contains a substrate which is a superficially porous refractory particle made up of discrete macroparticles with impervious non-porous cores, having joined thereto a coating of a series of sequentially adsorbed like monolayers of like inorganic microparticles. The core, in the form of a sphere, is of a diameter of between 5 and 500 microns and is composed of glass, although it may be of sand, ceramic or the like. Affixed to such core is a plurality of layers of microparticles which form an outer porous coating. The microparticles may range in size from 5 millimicrons to 1 micron. The microparticles may be amorphous silica, alumina, thoria, and the like. A preferred substrate is Zipax.

As described in such patents, the substrate has adhered thereto a polymer, preferably a water insoluble polymer, with such polymer being activated or provided with functional groups for covalent binding of the receptor. Such supports, as hereinabove noted, are more fully described in such patent or patent applications, and accordingly no further details are deemed necessary in this respect for a complete understanding of the present invention.

Alternatively, as described in U.S. Application Ser. No. 923711, filed concurrently herewith the solid support can be fibrous cotton and preferably mercerized absorbent cotton. The cotton may be activated with cyanogen bromide followed by covalent linking of the binder to the activated cotton.

The receptor or binder supported on the support is placed in a suitable flow through chamber for effecting binding of free $T_3$ tracer present in the sample. The assay is effected automatically employing automated equipment, providing for regeneration of the receptor, as described in detail in U.S. Pat. Nos. 3,896,217 and 4,009,005, which are hereby incorporated by reference.

More particularly, in accordance with the present invention, $T_3$ tracer, in particular radioiodinated $T_3$, is mixed with a serum sample or a reference serum sample, and the resulting mixture passed through the chamber containing $T_3$ receptor or binder; in particular $T_3$ antibody covalently bound to the particulate support. $T_3$ tracer which is not bound to $T_3$ binding protein; in particular, TBG, present in the sample, is bound to the binder in the chamber and $T_3$ tracer bound to serum proteins passes through the chamber. The radioactivity of the $T_3$ tracer which passes through the chamber is then counted.

Thereafter, the $T_3$ tracer bound to the immobilized receptor or binder in the chamber is released from the receptor by flowing an eluting solution therethrough to effect stoichiometric release of the $T_3$ tracer bound to the receptor. The radioactivity of the released tracer is then counted.

Following elution, the receptor is rinsed and then may be reused in the assay.

The percentage of $T_3$ tracer which was bound to the immobilized receptor or binder in the chamber is then determined; i.e., the ratio of $T_3$ eluted from the chamber to the sum of $T_3$ passing through the chamber and $T_3$ eluted from the chamber.

The percent binding of the $T_3$ tracer to the immobilized binder is inversely related to the serum protein binding capacity, and the binding capacity of a known serum sample is qualitatively determined by comparing the percentage of $T_3$ tracer bound in the unknown sample with the percentage of $T_3$ tracer bound in a reference sample. In order to minimize interassay variations, the assay is effected with both an unknown sample and a reference sample, with a normal pooled sample being assigned a percent uptake.

The percent uptake of the unknown sample ($T_3$ uptake) is determined as follows:

$$T_3 \text{ uptake} = \frac{\text{percent binding } T_3 \text{ tracer in unknown}}{\text{percent binding } T_3 \text{ tracer in reference}} \times \text{assigned percent uptake}$$

The thus determined $T_3$ uptake is a qualitative measurement of the serum binding capacity of the unknown, with such binding capacity showing a qualitative increase when the $T_3$ uptake is below the assigned percent uptake, and a qualitative decrease when the $T_3$ uptake is above the assigned percent uptake.

The invention will be further described in the following example; however, the scope of the invention is not to be limited thereby:

EXAMPLE

The reagents and equipment employed in the assay are as follows:

(a) The adsorption buffer used to introduce the sample is 0.02 M phosphate, pH 7.5 and 0.5 M sodium chloride.

(b) The eluting solution is 50% methanol in 0.1 M glycinate, pH 10.5.

(c) The rinse solution is stabilized distilled water.

(d) The sample buffer is 0.02 M phosphate, pH 7.5, 0.5 M sodium chloride and 0.01% bovine serum albumin.

(e) The tracer is $^{125}I$ labeled $T_3$ antigen, specific activity 3,000 mC/mg.

(f) The antibody is prepared using $T_3$ specific antibody raised in rabbits against triiodothyroproprionic acid conjugated to rabbit albumin.

The assay is effected with the antibody covalently linked to either cyanogen bromide, activated dextran coated Zipax or cyanogen bromide activated mercerized absorbent cotton gauze in automated equipment as described in U.S. Pat. No. 4,009,005, wich such apparatus being commercially available from Becton, Dickinson Immunodiagnostics, Automated Immunochemistry Systems. Such equipment is identified by the mark ARIA II.

The assay is effected employing both unknown sample and reference sample, and a self-contained computer shows the uptake in percent as normalized to the reference. The reference uptake is assigned a value of 30%.

The present invention is particularly advantageous in that it is possible to automatically qualitatively determine the thyroid hormone binding capacity of a serum sample. Moreover, such determination is effected in a rapid manner.

Numerous modifications and variations of the present invention are possible in light of the above teachings and, therefore, within the scope of the appended claims the invention may be practiced otherwise than as particularly described.

We claim:

1. An automated assay for qualitative determination of the thyroid hormone binding capacity of a serum sample, comprising:
    (a) mixing a known amount of $T_3$ tracer with an unknown serum sample;
    (b) flowing the mixture from step (a) through a chamber containing a $T_3$ binder supported on a solid support;
    (c) determining the amount of $T_3$ tracer which passes through the chamber;
    (d) flowing an eluting solution through the chamber to release any $T_3$ tracer which is bound to the binder in said chamber;
    (e) determining the amount of $T_3$ tracer released from the binder;
    (f) determining the percent of $T_3$ tracer present in the serum sample which was bound to the binder; and
    (g) comparing the percent of bound $T_3$ tracer in the sample with the percent of bound $T_3$ tracer in a reference sample to determine the difference in $T_3$ binding capacity between said sample and said reference sample to thereby qualitatively determine the $T_3$ binding capacity of said serum sample.

2. The assay of claim 1 wherein the $T_3$ tracer is labeled with a radioisotope.

3. The assay of claim 2 wherein the radioisotope is $^{125}I$.

4. The assay of claim 3 wherein the $T_3$ binder is an antibody to $T_3$.

5. The assay of claim 4 wherein the solid support is absorbent cotton and the antibody is covalently linked to cyanogen bromide activated absorbent cotton.

* * * * *